(12) United States Patent
Berry (10) Patent No.: US 9,820,897 B2
(45) Date of Patent: Nov. 21, 2017

(54) COMPOSITE LIQUID-RETENTIVE SUBSTRATE FOR A HYGIENE ARTICLE

(71) Applicant: Veronica Lee Berry, Snellville, GA (US)

(72) Inventor: Veronica Lee Berry, Snellville, GA (US)

(*) Notice: Subject to any disclaimer, the term of this patent is extended or adjusted under 35 U.S.C. 154(b) by 0 days.

(21) Appl. No.: 14/981,582

(22) Filed: Dec. 28, 2015

(65) Prior Publication Data

US 2017/0181903 A1    Jun. 29, 2017

(51) Int. Cl.
| A61F 13/15 | (2006.01) |
| A61F 13/537 | (2006.01) |
| A61F 13/53 | (2006.01) |
| A61F 13/494 | (2006.01) |
| A61F 13/535 | (2006.01) |

(52) U.S. Cl.
CPC .... *A61F 13/53752* (2013.01); *A61F 13/4946* (2013.01); *A61F 2013/53051* (2013.01); *A61F 2013/5355* (2013.01); *A61F 2013/530547* (2013.01); *A61F 2013/530985* (2013.01)

(58) Field of Classification Search
CPC .............. A61F 13/4753; A61F 13/4758; A61F 13/53051; A61F 13/530525; A61F 13/530547; A61F 13/530562; A61F 13/475; A61F 13/530948; A61F 13/53097; A61F 13/4946; A61F 13/49426; A61F 13/5326; A61F 13/535; A61F 13/5355; A61F 13/530262; A61F 13/53027; A61F 13/503277; A61F 13/53445; A61F 13/530437; A61F 13/530445; A61F 13/4755
See application file for complete search history.

(56) References Cited

U.S. PATENT DOCUMENTS

| D83,337 | S | * | 2/1931 | Mink | D24/126 |
| 4,212,302 | A | * | 7/1980 | Karami | A61F 13/49406 604/368 |
| 4,573,988 | A | * | 3/1986 | Pieniak | A61F 13/534 604/379 |
| 4,731,071 | A | * | 3/1988 | Pigneul | A61F 5/4401 604/368 |
| 4,738,675 | A | * | 4/1988 | Buckley | A61F 5/4401 604/358 |
| 5,019,063 | A | * | 5/1991 | Marsan | A61F 13/15203 604/368 |

(Continued)

FOREIGN PATENT DOCUMENTS

| IT | EP 0455607 A1 * 11/1991 | ......... A61F 13/5323 |
| JP | WO 2005089690 A1 * 9/2005 | ............... A41B 9/12 |

*Primary Examiner* — Bradley Philips
(74) *Attorney, Agent, or Firm* — Michael Drew (57) ABSTRACT

A composite liquid-retentive substrate for a hygiene article comprises a base layer of first liquid-absorptive material. The base layer having a posterior end and a diametrically opposed anterior end interconnected by an intermediate tapered region. The posterior end has opposing posterior corners and the anterior end has opposing anterior corners. A posterior liquid-flow abutment comprising second absorptive material is disposed substantially around a perimeter of the posterior end. At least one anterior liquid-flow abutment comprising second absorptive material is disposed proximate one of the anterior corners of the anterior end.

3 Claims, 6 Drawing Sheets

(56) References Cited

U.S. PATENT DOCUMENTS

| Patent/Pub. No. | | Date | Inventor | Class |
|---|---|---|---|---|
| 5,087,506 | A * | 2/1992 | Palumbo | A61F 13/532 428/192 |
| 5,151,091 | A * | 9/1992 | Glaug | A61F 13/4756 604/378 |
| 5,248,524 | A * | 9/1993 | Soderlund | A61F 13/15658 118/308 |
| D341,199 | S | 11/1993 | Huguley | |
| 5,262,223 | A * | 11/1993 | Palumbo | A61F 13/535 428/195.1 |
| 5,300,565 | A * | 4/1994 | Berg | A61L 15/60 525/54.2 |
| 5,348,547 | A * | 9/1994 | Payne | A61F 13/49009 604/378 |
| 5,356,403 | A * | 10/1994 | Faulks | A61F 13/534 604/358 |
| 5,415,716 | A * | 5/1995 | Kendall | A61F 13/15804 156/256 |
| 5,422,169 | A * | 6/1995 | Roe | A61L 15/18 428/212 |
| 5,429,633 | A | 7/1995 | Davis et al. | |
| 5,505,718 | A * | 4/1996 | Roe | A61F 13/535 604/368 |
| 5,539,019 | A * | 7/1996 | Suskind | A61F 13/534 428/407 |
| 5,547,745 | A * | 8/1996 | Hansen | A61L 15/60 428/378 |
| 5,599,336 | A * | 2/1997 | Plischke | A61F 13/534 604/358 |
| 5,741,241 | A * | 4/1998 | Guidotti | A61F 13/49009 604/368 |
| 5,817,079 | A * | 10/1998 | Bergquist | A61F 13/15626 428/299.1 |
| 5,827,254 | A * | 10/1998 | Trombetta | A61F 13/47 604/378 |
| 5,830,296 | A * | 11/1998 | Emenaker | A61F 13/15 156/209 |
| 5,855,571 | A * | 1/1999 | Steger | A61L 15/60 604/368 |
| 5,873,870 | A * | 2/1999 | Seitz | A61F 13/49007 604/385.04 |
| 5,961,506 | A * | 10/1999 | Guidotti | A61F 13/532 604/378 |
| 5,993,431 | A | 11/1999 | McFall et al. | |
| 6,383,960 | B1 * | 5/2002 | Everett | A61F 13/535 442/317 |
| 6,437,214 | B1 * | 8/2002 | Everett | A61F 13/15203 604/378 |
| 6,441,268 | B1 * | 8/2002 | Edwardsson | A61F 13/532 604/378 |
| 6,459,016 | B1 * | 10/2002 | Rosenfeld | A61F 13/533 428/221 |
| 6,465,710 | B1 * | 10/2002 | Annergren | A61F 13/15203 604/368 |
| 6,498,283 | B1 * | 12/2002 | Wada | A61F 13/4946 604/358 |
| 6,592,561 | B2 | 7/2003 | Simard et al. | |
| D500,131 | S | 12/2004 | Choice | |
| D631,958 | S * | 2/2011 | Marcelo | D24/125 |
| D679,004 | S | 3/2013 | Norman et al. | |
| 9,468,566 | B2 * | 10/2016 | Rosati | A61F 13/535 |
| 2002/0019614 | A1 * | 2/2002 | Woon | A61F 13/4756 604/358 |
| 2002/0193728 | A1 * | 12/2002 | Infantino | A61F 13/49466 604/25 |
| 2003/0100873 | A1 * | 5/2003 | Hermansson | A61F 13/15203 604/374 |
| 2003/0114810 | A1 | 6/2003 | Weber | |
| 2003/0120233 | A1 * | 6/2003 | Ohshima | A61F 13/4752 604/369 |
| 2003/0135177 | A1 * | 7/2003 | Baker | A61F 13/15634 604/368 |
| 2003/0236510 | A1 * | 12/2003 | Yasumura | A61F 13/15626 604/367 |
| 2004/0059018 | A1 * | 3/2004 | Gagliardi | A61F 13/53 523/111 |
| 2004/0254549 | A1 * | 12/2004 | Olson | A61F 13/42 604/361 |
| 2004/0254555 | A1 * | 12/2004 | Wang | A61F 13/532 604/385.01 |
| 2005/0215967 | A1 * | 9/2005 | Toro | A61F 13/4755 604/378 |
| 2006/0173434 | A1 * | 8/2006 | Zoromski | A61F 13/53 604/374 |
| 2008/0312620 | A1 * | 12/2008 | Ashton | A61F 13/15634 604/366 |
| 2010/0004614 | A1 * | 1/2010 | Ashton | A61F 13/532 604/367 |
| 2012/0310195 | A1 * | 12/2012 | Toda | A61F 13/535 604/369 |
| 2013/0096525 | A1 * | 4/2013 | Hermansson | A61F 13/471 604/369 |
| 2013/0281949 | A1 * | 10/2013 | Periman | A61L 15/20 604/361 |
| 2013/0331806 | A1 * | 12/2013 | Rosati | A61F 13/53 604/366 |

\* cited by examiner

Fig_1

Fig_2

COMPOSITE LIQUID-RETENTIVE SUBSTRATE FOR A HYGIENE ARTICLE

RELATED APPLICATIONS

N/A

TECHNICAL FIELD

This invention relates to a composite liquid-retentive substrate for a hygiene article. More particularly, the invention relates to a composite liquid-retentive substrate for a feminine hygiene article such as a sanitary napkin or feminine hygiene pad.

BACKGROUND OF THE INVENTION

Uncontrolled liquid flow from the crotch region of individuals is problematic because the individual's underpants can be soiled by the liquid. In this regard, women's menstrual flow is particularly problematic because blood stains in underpants are very undesirable and, further, can easily leak through the underpants to stain outer clothing.

Many solutions have been devised over the years to address the matter of leakage of menstrual flow to undergarments and outer clothes. Solutions have included articles such as tampons and so-called sanitary napkins. More modern-day articles such as feminine hygiene pads have been produced in various configurations to address the problem of soiled underpants and outer clothing. The results of the various solutions have been mixed, whereas some solutions have been more successful than others.

A particular menstrual liquid-flow problem that has been difficult to address is the problem of women that have above-average menstrual flow. That is, a menstrual flow that is so copious during a short period of time that it cannot be adequately retained by typical products. Blood issuing in these situations often seeps around edges of even the most effective pads or sanitary napkins.

Seepage along the rear edge of a hygiene pad or sanitary napkin is problematic because liquid captured in a hygiene pad or napkin can be forced outwardly of the rear edge when an individual sits. This is because when an individual sits, the rear end of the individual in conjunction with the sitting surface creates a pressure that forces liquid (blood) captured in the pad or napkin outwardly of the rear perimeter of the pad. Seepage at the front end of a pad often occurs because liquid (blood) tends to flow along the crease at the joinder of the upper thigh and abdomen because of pressure created when an individual is engaged in movement or sitting that presses the thigh and abdomen together.

Thus, it can be appreciated that it would be useful to have a means for preventing the soiling of underpants of individuals having a crotch-originating liquid flow such as menstrual blood flow that is difficult to retain by typical means.

SUMMARY OF THE INVENTION

A composite liquid-retentive substrate for a hygiene article according to a broad aspect of the invention comprises a base layer of liquid-absorptive material, the base layer having a posterior end and a diametrically opposed anterior end interconnected by an intermediate tapered region. The posterior end has opposing posterior corners and the anterior end has opposing anterior corners. A posterior liquid-flow abutment comprising second absorptive material is disposed substantially around a perimeter of the posterior end. At least one anterior liquid-flow abutment also comprising a second absorptive material is disposed at one of the anterior corners of the anterior end. In one embodiment, the liquid-flow abutments are affixed to an upper surface of the base layer. In a second embodiment, the liquid-flow abutments are integrally formed with the base layer.

DETAILED DESCRIPTION

Embodiments of the present invention are described in this section. The disclosed embodiments are merely exemplary of the invention that may be embodied in various and alternative forms, and combinations thereof. As used herein, the word "exemplary" is used expansively to refer to embodiments that serve as illustrations, specimens, models, or patterns. The figures are not necessarily to scale and some features may be exaggerated or minimized to show details of particular components. In other instances, well-known components, systems, materials, or methods have not been described in detail in order to avoid obscuring the present invention. Therefore, specific structural and functional details disclosed herein are not to be interpreted as limiting, but merely as a basis for the claims and as a representative basis for teaching one skilled in the art to variously employ the present invention.

Referring now to the drawings, wherein like numerals indicate like elements throughout the several views, the drawings illustrate certain of the various aspects of exemplary embodiments.

As an overview, the invention provides a composite liquid-retentive substrate for a hygiene article according to a broad aspect of the invention. The substrate comprises a base layer of a first liquid-absorptive material with additional liquid absorptive material strategically disposed with respect to the base layer to inhibit flow of liquid captured in the base layer. A posterior liquid-flow abutment is strategically disposed around the posterior end of the base layer. Anterior liquid-flow abutments are strategically disposed at anterior corners of the base layer.

Figure 1:
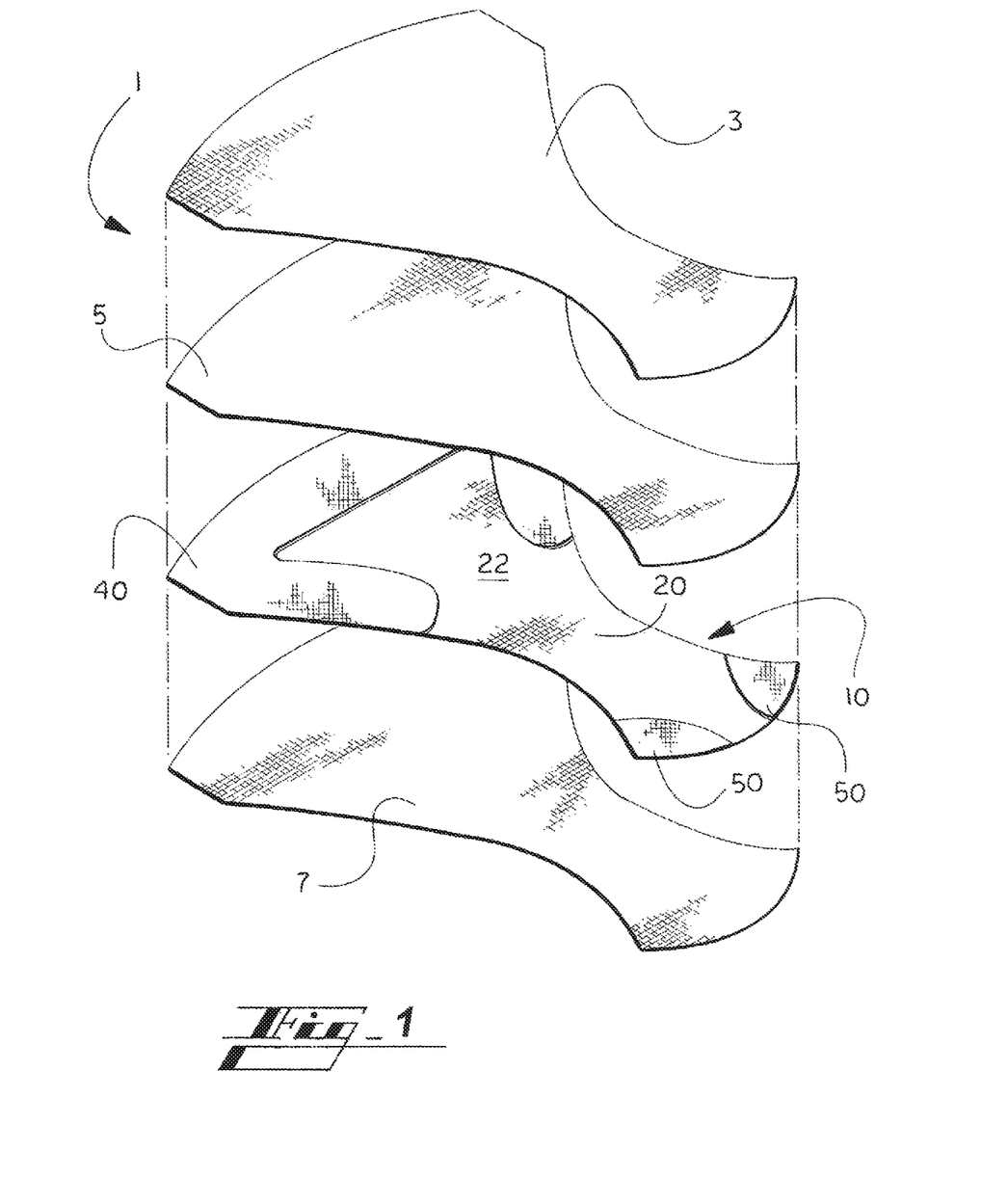
FIG. 1 is a perspective illustration of an embodiment of a composite liquid-retentive substrate for a hygiene article in accordance with the teachings of the present invention, juxtaposed with additional layers of a feminine hygiene pad.

Referring first to FIG. 1, therein is illustrated in perspective view a composite liquid-retentive substrate 10 for a hygiene article according to an embodiment of the invention. The composite substrate is shown in an exploded illustration of a hygiene pad 1 into which the substrate 10 is suitably incorporated. The composite substrate 10 includes a base layer 20, a posterior liquid-flow abutment 40 and a pair of opposing anterior liquid-flow abutments 50. The topmost surface 22 of the base layer 20 is shown. The substrate 10 is shown juxtaposed with additional layers of a feminine hygiene pad 1. The pad 1 contains, from top to bottom, a liquid permeable layer as a top-most sheet 3, an intermediate liquid-permeable sheet 5, the composite substrate 10 in accordance with an embodiment of the invention and a liquid-impervious layer as the bottom-most sheet 7.

Figure 2:
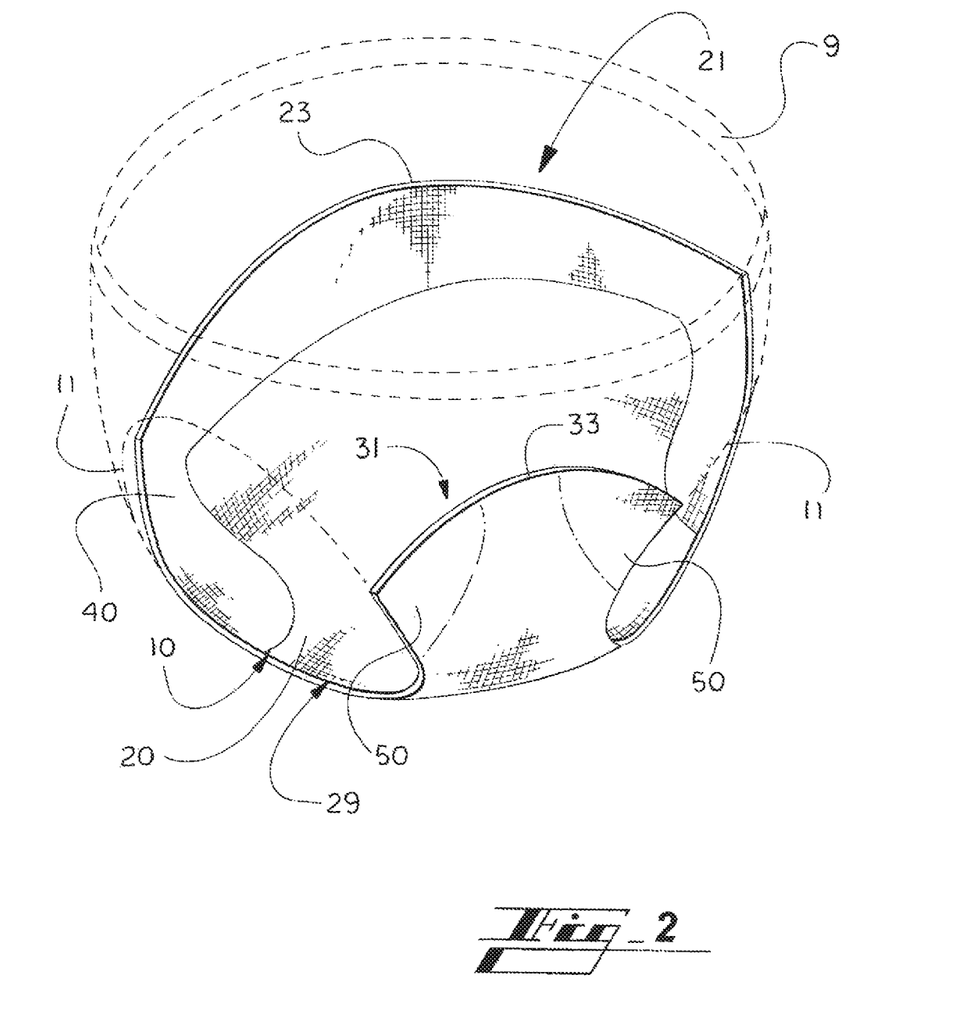
FIG. 2 is a perspective illustration of a liquid-retentive substrate disposed within a pair of underpants without the other layers of a hygiene pad so that alignment of the substrate with respect to the underpants can be seen.

FIG. 2 is a perspective illustration of an embodiment of a composite substrate 10 of the invention alone (that is, without the other sheets of the environment of a feminine hygiene pad that are illustrated in FIG. 1) disposed for use within a pair of underpants 9. The underpants 9 are shown in phantom view by dash lines. A posterior end 21 and a diametrically opposed anterior end 31 are interconnected by a tapered intermediate region 29. A posterior edge 23 helps define the boundary of the posterior end 21 and an anterior edge 33 helps define the boundary of the anterior end 31. The posterior liquid-flow abutment 40 is shown disposed at the posterior end of the base layer 20 and anterior liquid-flow abutments 50 are shown disposed at the anterior end of the base layer 20. The tapered intermediate region 29 that interconnects the posterior end 21 and the anterior end 31 of the base layer 20 is shown in substantial alignment with leg openings 11 of the underpants proximate the lower crotch region of the underpants 9.

Figures 3, 4, 5, 6:
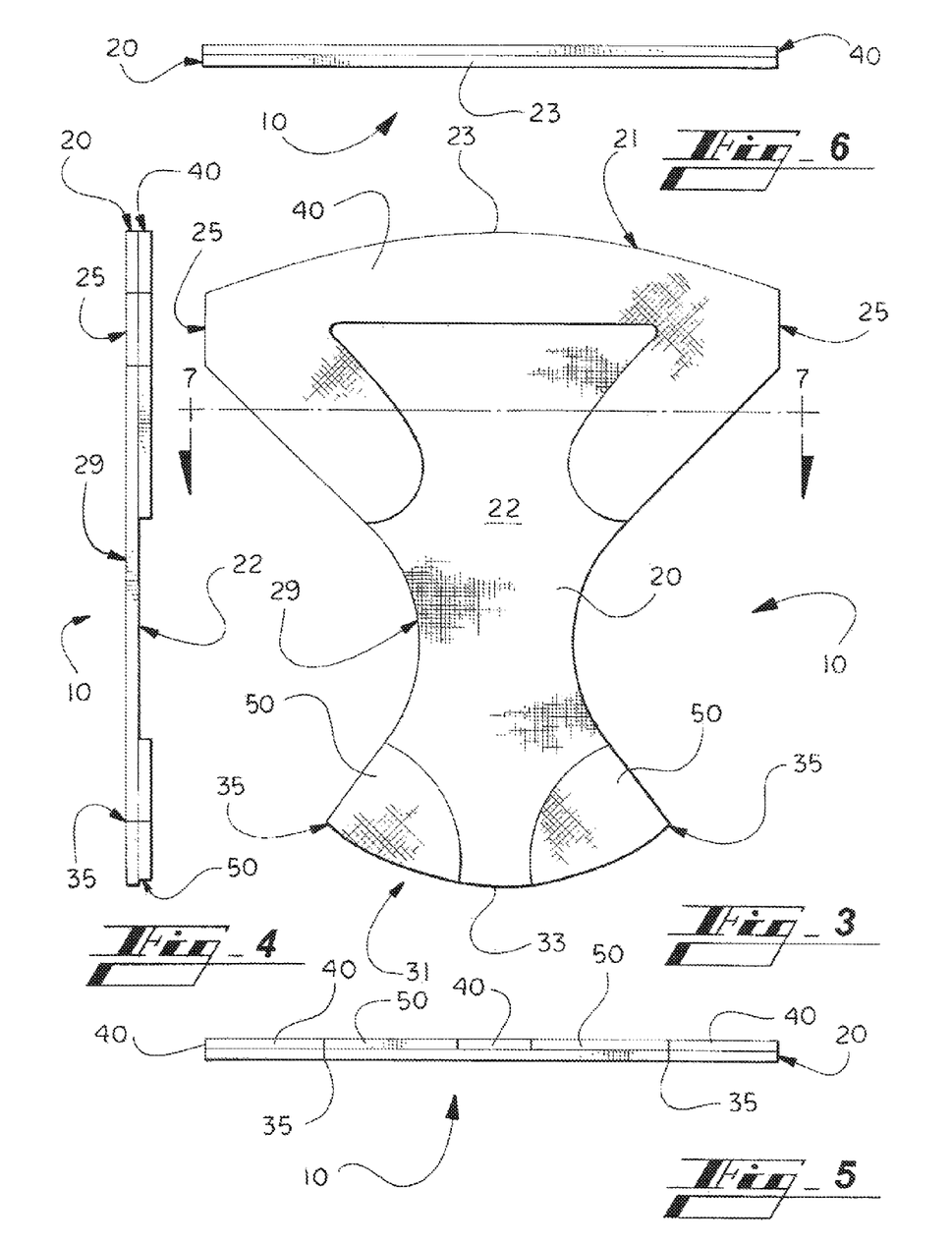
FIG. 3 is a top plan view of a first embodiment of a composite liquid-retentive substrate for a hygiene article in accordance with the teachings of the present invention.
FIG. 4 is a side elevation view of the substrate of FIG. 3.
FIG. 5 is a front elevation view of the substrate of FIG. 3.
FIG. 6 is a rear elevation view of the substrate of FIG. 3.

Referring now to FIG. 3, therein is shown a first embodiment of a composite liquid-retentive substrate 10 for a hygiene article according to a first embodiment of the invention in a top plan view. The substrate 10 comprises a base layer 20 of liquid-absorptive material. In the top plan view, the upper surface 22 of the base layer 20 is shown. The base layer 20 has a posterior end 21 and an opposing anterior end 31 that are interconnected by an intermediate tapered region 29. In the embodiment, the posterior end 21 is wider than the anterior end 31. The posterior end 21 encompasses more surface area than the anterior end 31 because it is configured to conform to the rear end of a user of a sanitary pad into which the composite substrate 10 would be incorporated. The posterior end 21 is defined in-part by a posterior edge 23 interconnecting opposing posterior corners 25. The posterior end 21 has a substantially triangular configuration which generally conforms to the rear-end configuration of the body of an individual. Although the posterior edge 23 can be straight, the curved edge shown facilitates a more complementary fit with respect to a rear-end and/or lower-back region of an individual when the substrate 10 is used in a hygiene pad. An average individual has at least a slightly curved rear end and/or lower back area with which the curved edge 23 would be at least slightly more accommodating than a straight edge to provide a better fit when the substrate 10 is in use. The anterior end 31 is defined in-part by an anterior edge 33 interconnecting opposing anterior corners 35. The anterior end 31 has a substantially triangular configuration which conforms to the generally wedge-shaped configuration of a crotch of an individual. Although the anterior edge 33 can be straight, the curved edge shown facilitates a more complementary fit with an abdomen region of an individual when the substrate 10 is used in a hygiene pad. An average individual has at least a slightly protruding abdomen with which the curved edge 31 would be at least slightly more accommodating than a straight edge in providing a better fit when the substrate 10 is in use.

A posterior liquid-flow abutment 40 is disposed around a perimeter of the posterior end 21 of the base layer 20. Because the posterior end 21 is substantially triangular shaped, the abutment 40 is designed in a similar configuration that is open at the apex of the triangular configuration proximate the tapered region 29 resulting in a somewhat inverted U-shaped configuration for the posterior abutment 40.

Each anterior liquid-flow abutment 50 is designed to overlie the corner region of a pad that incorporates the composite substrate 10 of the invention. Thus each anterior liquid-flow abutment 50 has a substantially triangular shape that corresponds to corners of the substantially triangular-shaped anterior end 33 of the base layer 20.

Although a single anterior liquid-flow abutment can be used along the perimeter of the anterior end 31 of the base layer within the teachings of the invention, in the embodiment of FIG. 3 individual anterior liquid-flow abutments 50 are disposed at respective corners of the anterior end 31 of the base layer 20 such that liquid-flow inhibition is focused at the region of joinder of an individual's thigh and abdomen when a hygiene pad incorporating the substrate 10 used. The corners of the anterior end 31 are strategically designed to overlie these critical crease lines where the thigh and abdomen intersect. The crease formed at the joinder of the thigh and abdomen is the path along which liquid (blood) is likely to travel when the base layer 20 has become substantially ladened with liquid (blood).

Referring now to FIG. 4, therein is illustrated a side elevation view of the composite substrate 10 of FIG. 3. In this view, alignment of the posterior liquid-flow abutment 40 and anterior liquid-flow abutment 50 disposed upon the top surface 22 of the base layer 20 can be seen further. In addition, alignment of the posterior liquid-flow abutment 40 in relation to posterior corner 25 of the base layer 20 and alignment of the anterior liquid-flow abutment 50 in relation to anterior corner 35 of the base layer 20 can be seen.

Referring now to FIG. 5, therein is illustrated a front elevation view of the composite substrate 10 of FIG. 3. In this view, another viewpoint of alignment of the posterior liquid-flow abutment 40 and anterior liquid-flow abutment 50 with respect to the base layer 20 can be seen. In addition, another viewpoint of alignment of both anterior liquid-flow abutments 50 with respect to respective corners 35 of the base layer 20 can be seen.

Referring now to FIG. 6, therein is illustrated a rear elevational view of the composite substrate 10 of FIG. 3. In this view, the posterior edge 23 of the base layer 20 in alignment with the posterior liquid-flow abutment 40 can be seen.

Figure 7:
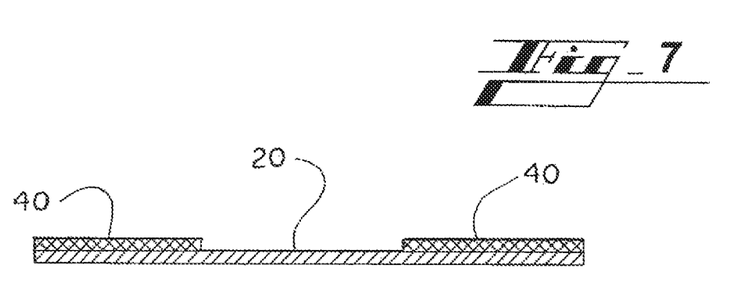
FIG. 7 is a sectional view of the substrate of FIG. 3 taken along line 7-7 of FIG. 3.

Referring now to FIG. 7, therein is illustrated a cross-section of the composite substrate of FIG. 3 taken along line 7-7 of FIG. 3. This view further illustrates the alignment and adjacent disposition of the posterior liquid-flow abutment 40 with respect to the base layer 20. The alignment and disposition of the anterior liquid-flow abutments 50 with respect to the base layer 20 cannot be seen in this view but are similar to the alignment and disposition of posterior features.

Figure 8:
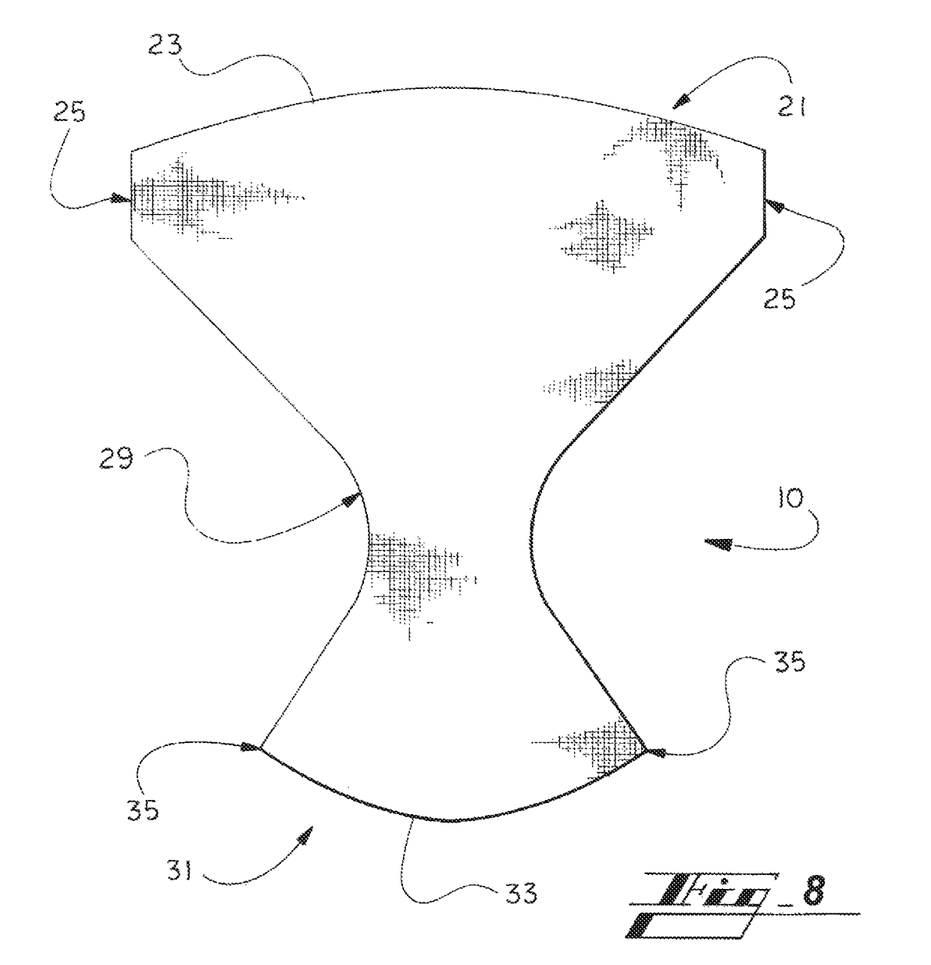
FIG. 8 is bottom plan view of the substrate of FIG. 3.

Referring now to FIG. 8, the bottom surface 24 of the base layer 20 of the composite substrate 10 of FIG. 3 is shown in bottom plan view. Many of the features described in relation to FIG. 3 are also shown in this view, such as the posterior end 21, posterior edge 23 and posterior corners 25 of the base layer 20; the anterior end 31, anterior edge 33 and anterior corners 35 of the base layer 20; and the tapered region 29 interconnecting the posterior end 21 and anterior end 31.

Figures 9, 10, 11, 12, 13:
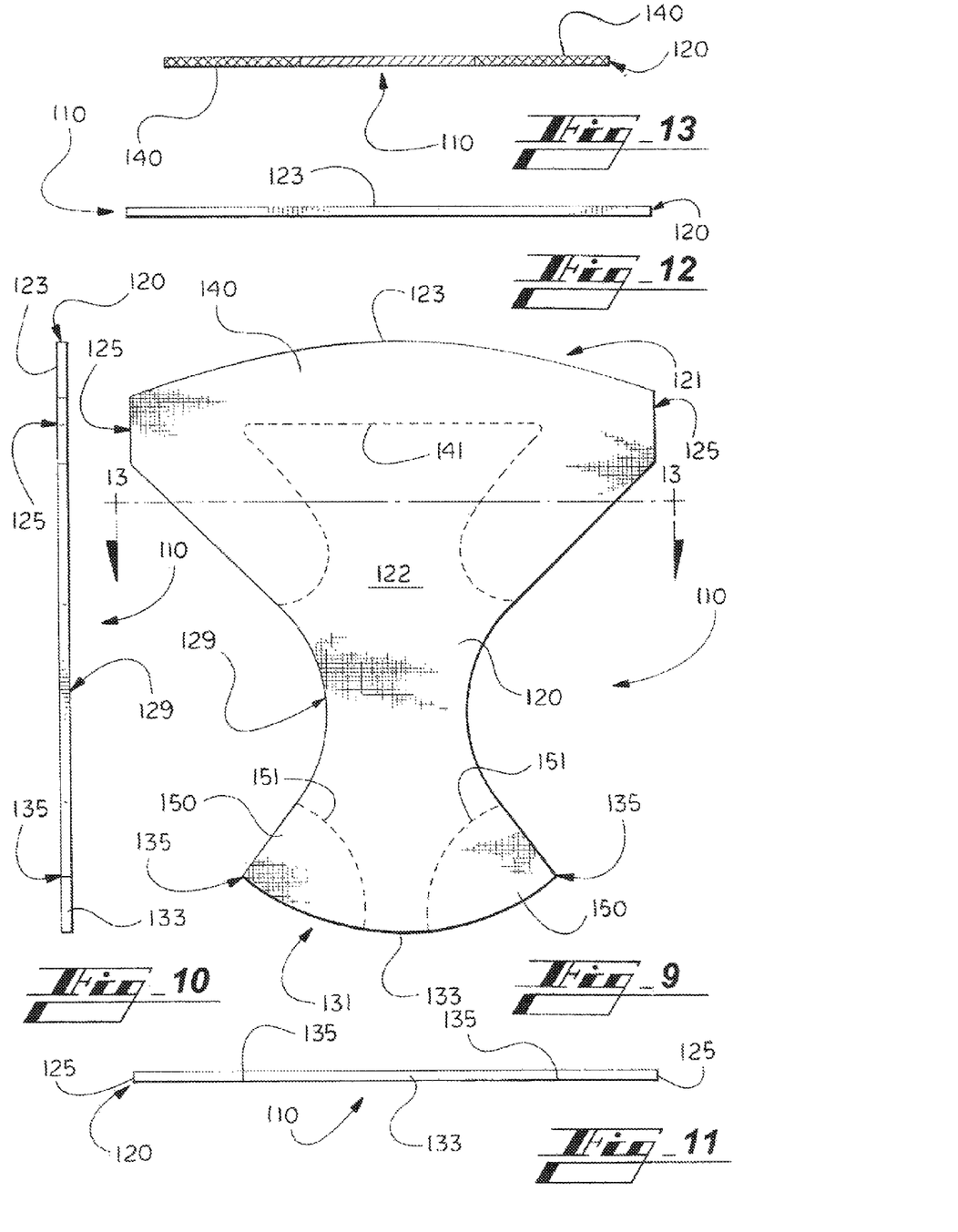
FIG. 9 is a top plan view of a second embodiment of a composite liquid-retentive substrate for a hygiene article in accordance with the teachings of the present invention.
FIG. 10 is a side elevation view of the substrate of FIG. 9.
FIG. 11 is a front elevation view of the substrate of FIG. 9.
FIG. 12 is rear elevation view of the substrate of FIG. 9.
FIG. 13 is a sectional view of the substrate of FIG. 9 taken along line 11-11 of FIG. 9.

Referring now to FIG. 9, therein is illustrated in top plan view a second embodiment of a composite liquid-retentive substrate 110 for a hygiene article in accordance with the teachings of the present invention. The top plan view shows the top surface 122 of the base layer 120. Similar to the embodiment of FIG. 3, in this embodiment of FIG. 9, a base layer 120 comprising liquid-absorptive material has a posterior end 121 defined in-part by a posterior edge 123 extending between posterior corners 125. An anterior end 131 is defined in-part by an anterior edge 133 extending between anterior corners 135. An intermediate tapered region 129 extends between and interconnects the posterior end 121 and the anterior end 131. The composite substrate 110 of the second embodiment of FIG. 9 differs from the embodiment of FIG. 3 in that a posterior liquid-flow abutment 140 and anterior liquid-flow abutments 150 are integrally formed with the base layer 120 in the second embodiment rather than being distinct elements disposed upon the upper surface of the base layer as in the first embodiment. The posterior liquid-flow abutment 140 is integrally formed in the base layer 120 around a perimeter of the posterior end 121 and is demarked by the hidden line 141. Each anterior liquid-flow abutment 150 is integrally formed in the base layer 120 and is demarked by the hidden lines 151. The abutments 140, 150 of the composite substrate 110 of the second embodiment are positioned in the same locations with respect to the edges 123, 133 and corners 125, 135 of the base layer 120 of the second embodiment as the abutments 40, 50 of the composite substrate 10 of the first embodiment are positioned with respect to the edges 23, 33 and corners 25, 35 of the base layer 20 of the first embodiment.

Referring now to FIG. 10, therein is illustrated a side elevation view of the composite substrate 110 of FIG. 9. In this view, a posterior corner 125, the posterior edge 123, an anterior corner 135, the anterior edge 133 and an edge of the intermediate tapered region 129 of the base layer 120 can be seen.

Referring now to FIG. 11, therein is illustrated a front elevation view of the composite substrate 110 of FIG. 9. In this view, the posterior corners 125, anterior corners 135 and front edge 133 of the base layer 120 can be seen.

Referring now to FIG. 12, therein is illustrated a rear elevation view of the composite substrate 110 of FIG. 9. In this view, the posterior edge 123 of the base layer 120 can be seen.

Referring now to FIG. 13, therein is illustrated a cross-sectional view of the substrate of FIG. 9 taken along line 13-13 of FIG. 9. In this view, a cross section of the posterior liquid-flow abutment 140 that is integrally formed with the base layer 120 can be seen. As previously noted, each anterior liquid-flow abutment 150 is similarly integrally formed with the base layer 120.

Figures 14, 15, 18:
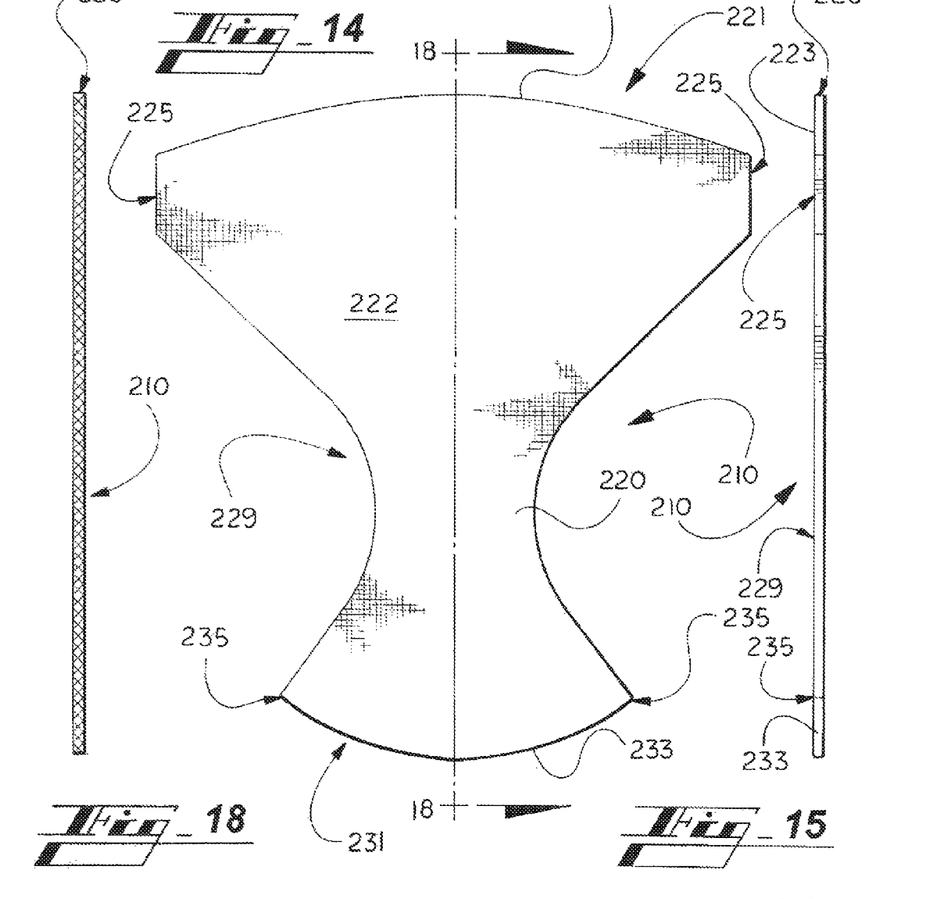
FIG. 14 is a top plan view of a third embodiment of a composite liquid-retentive substrate for a hygiene article in accordance with the teachings of the present invention.
FIG. 15 is a sectional view of the substrate of FIG. 14 taken along line 15-15 of FIG. 14.
FIG. 18 is side elevation view of the substrate of FIG. 14.

Referring now to FIG. 14, therein is illustrated in top plan view a third embodiment of a composite liquid-retentive substrate 210 for a hygiene article in accordance with the teachings of the present invention. This top plan view shows the top surface 222 of the base layer 220. Similar to the embodiments of FIGS. 3 and 9, the base layer 220 has a posterior end 221 defined by a posterior edge 223 extending between posterior corners 225. An anterior end 231 is defined by an anterior edge 233 extending between anterior corners 235. An intermediate tapered region 229 extends between and interconnects the posterior end 221 and the anterior end 231. The composite substrate 210 of the third embodiment of the invention that is shown in FIG. 14 differs from the first embodiment shown in FIG. 3 and the second embodiment shown in FIG. 9 in that the entire base layer 220 is infused with a material that enhances the absorptivity of the base layer 220 including the strategic areas at the posterior end and anterior corners.

Referring now to FIG. 15, therein is illustrated a side elevation view of the composite substrate 210 of FIG. 14. In this view, a posterior corner 225, the posterior edge 223, an anterior corner 235, the anterior edge 233 and an edge of the intermediate tapered region 229 of the base layer 220 can be seen.

Figure 16:
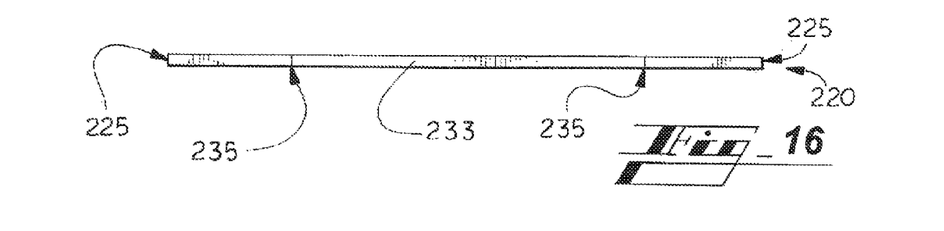
FIG. 16 is a front elevation view of the substrate of FIG. 14.

Referring now to FIG. 16, therein is illustrated a front elevation view of the composite substrate 210 of FIG. 14. In this view, the posterior corners 225, anterior corners 235 and front edge 233 of the base layer 220 can be seen.

Figure 17:
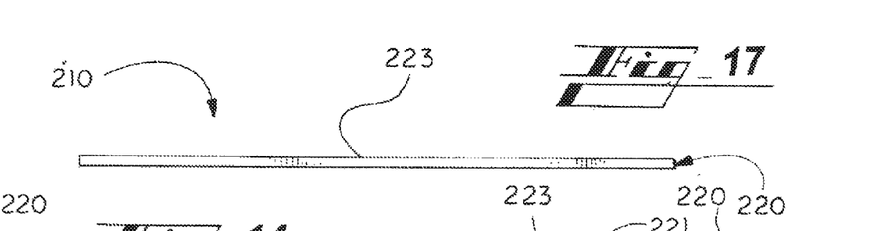
FIG. 17 is rear elevation view of the substrate of FIG. 14.

Referring now to FIG. 17, therein is illustrated a rear elevation view of the composite substrate 210 of FIG. 14. In this view, the posterior edge 223 of the base layer 220 can be seen.

Referring now to FIG. 18, therein is illustrated a cross-sectional view of the substrate of FIG. 14 taken along line 18-18 of FIG. 14. In this view, the interior of fully-infused (or impregnated) base layer 220 can be seen.

Referring now back to the first and second embodiments and the illustrations therefor, the posterior abutment 40 and the anterior abutments 50 are formed from liquid-absorptive material. Preferably, in the first and second embodiments of the invention described herein, the abutments 40, 50, 140, 150 have a higher degree of liquid absorbency than the base layer 20 so that liquid (such as blood) is held in the absorbent material of the base layer 20, 120 while the respective abutments 40, 50, 140, 150 inhibit liquid flow beyond the areas and points where the abutments 40, 50, 140, 150 are disposed in relation to the base layer 20, 120.

To help distinguish the two materials employed in the first embodiment of the invention, the material comprising the base layer is referred to herein as a first absorptive material while the material comprising the abutments 40, 50 is referred to herein as a second absorptive material.

Although there are many liquid-absorptive materials that may be used to form the base layer 10 and abutments 40, 50 of the first embodiment and the base layer 120 and abutments 140, 150 of the second embodiment, materials that absorb and retain blood are especially useful in employing the invention. A particularly suitable composition for the base layer 20 of the first embodiment, that is, a first liquid-absorptive material, is a commercially-available product sold under the trademark NOVATHIN®. NOVATHIN is manufactured by EAM Corp having an address of 2075 Sunset Blvd, Jesup, Ga. 31545, United States of America. A second liquid-absorptive material can be a material that is completely distinct from the first liquid-absorptive material. However, the invention teaches and contemplates that a suitable second absorptive material can be a liquid-absorptive material similar to or identical to the first liquid-absorptive material but infused (which may also be considered impregnated) with an absorptive additive that increases the absorptivity of the host absorptive material (that is, the material that is infused). Thus the invention contemplates and teaches that the second liquid-absorptive material can be a first absorptive material infused (or impregnated) with an absorptive additive. An example of a suitable second liquid-absorptive material of the nature described is NOVATHIN infused with a commercially-available absorptive additive sold under the trademark AQUA SORB®. AQUA SORB is manufactured by ARK Enterprises, a company having an address of 807 Bridle Trail Lane, Peculiar, Mo. 64078, United States of America.

As described above with respect to the second embodiment of a composite liquid-retentive substrate 110 according to the invention illustrated in FIGS. 9 through 13, the invention teaches a base layer of two types of liquid-absorbent materials, that is, a first liquid-absorbent material comprising the base layer 120 in general with the posterior abutment 140 and anterior abutments 150 comprising a second liquid-absorbent material integrally formed with the first liquid-absorbent material. As in the case of the first embodiment, although the first and second liquid absorbent materials can be completely distinct and dis-similar liquid-absorbent materials, the invention contemplates and teaches a first liquid-absorbent material that forms the entire base layer 120 while the abutments 140, 150 are integrally formed by infusion of an absorbent additive in the strategic posterior and anterior portions of the base layer 120. Suitable first and second liquid-absorbent materials are the same as those described for the first embodiment. A suitable absorbent additive is the same as that described herein with respect to the first embodiment.

With respect to the third embodiment of a composite liquid-retentive substrate 210 in accordance with the teachings of the invention as described above, the invention teaches extension of enhanced absorbency throughout the base layer 220 resulting in an absorbency-enhanced base layer 220. The invention teaches that the absorbency-enhanced base layer 220 may be combined with the externally attached abutments 40, 50 as taught by the first embodiment to form an embodiment of an enhanced composite liquid-retentive substrate for a hygiene article having the appearance of the substrate illustrated in FIGS. 3-8. Similarly, the invention teaches that the absorbency-enhanced base layer 220 may be combined with the integrally-formed abutments 140, 150 as taught by the second embodiment to form another embodiment of an enhanced composite liquid-retentive substrate for a hygiene article having the appearance of the substrate illustrated in FIGS. 9-13.

The invention contemplates and teaches that the posterior liquid-flow abutment 40 and anterior liquid-flow abutments 50 of the first embodiment of the invention can be affixed to the top surface 22 of the base layer 20 by any suitable means of attaching materials of the types described above to one another. For example, the posterior liquid-flow abutment 40 and anterior liquid-flow abutments 50 may be affixed to the top surface 22 of the base layer 20 through use of an adhesive.

The bottom surface 24 of only the first embodiment of the composite substrate of FIG. 3 is illustrated because the features of the bottom surfaces of the embodiments of FIG. 9 and FIG. 14 do not significantly vary from those of the bottom surface 24 of FIG. 3 so to as warrant separate illustration.

The posterior liquid-flow abutment 40 provides a barrier that inhibits the flow of liquids (such as blood) that are captured in the base layer from flowing to the posterior edge 23 of the base layer 20 and escaping a hygiene pad, thus lessening the likelihood of soiling undergarments or outer clothing. The anterior liquid-flow abutments 50 provide barriers that inhibit the flow of liquids (such as blood) that are captured in the base layer 20 from flowing to the corner 35 regions of the base layer 20 and escaping a hygiene pad, thus lessening the likelihood of soiling underpants or clothing. The abutments 40, 50 are strategically located with respect to the base layer 20 so that when the substrate 10 is employed as part of a hygiene pad, a seal is formed between an individual's body and the abutments to help inhibit undesirable liquid (blood) flow. Placement of the posterior abutment 50 as a substantially U-shaped barrier disposed around a substantially triangular-shaped posterior end 21 helps facilitate forming a seal with the back-side area of an individual's body. The triangular-shaped anterior abutments 50 strategically disposed at vertices of the substantially triangular-shaped anterior end 31 help facilitate formation of a seal at the crease line of joinder between thigh and abdomen. In the third embodiment of FIG. 14 the entire base layer 220 is essentially a fortified or reinforced substrate 210 that provides sealing and liquid-flow inhibition at the areas of concern The posterior liquid-flow abutment 140 and anterior liquid-flow abutments 150 of the second embodiment of the invention as illustrated in FIGS. 9-13 are disposed and function in much the same manner as the abutments 40, 50 of the first embodiment of FIGS. 3-8. There is a structural distinction between the first and second embodiments in that in the first embodiment the abutments 40, 50 present raised elements that are also more absorbent than the remainder of the base layer 20 in general. In the second embodiment, the abutments 140, 150 may not appreciably extend above the surface of the base layer 120, if at all. However, the abutments 140, 150 will be more absorbent than the uninfused portions of the base layer 120.

Referring now back to FIG. 1, an embodiment of a hygiene pad 1 constructed in accordance with the teachings of the invention has multiple plies of material. The top-most ply 3 is designed to lie adjacent to and be in contact with the body of an individual. The top-most ply 3 comprises liquid-permeable material that draws liquid, such as blood, emanating from the crotch region of an individual into the sheet 3 and then allows it to pass through the ply 3 onto the succeeding adjacent sheet. A suitable material for the top-most ply 3 is a sheet of polypropylene material that is commercially-available from Avanti Manufacturing, 1580 Corporate Parkway Blvd, Clarksville, Tenn. The selected product is described by the Avanti company as 30 grams of spunbond polypropylene that is hydrophilic (that is, tending to absorb liquid) in nature. A second ply 5, which lies adjacent the top-most ply 3, is also a liquid-permeable ply which for convenience is considered an intermediate liquid-permeable ply. The second ply may be considered an "acquisition layer" as that term is used in the feminine hygiene napkin art. A suitable material for the second ply is a product described as thermally-fusible bi-component fibers and cellulose as sold by Glatfelter, 96 South George Street, York, Pa. 17401. The third ply is the composite liquid-retentive substrate 10, 110, 210 as taught by the invention. The last ply, that is, the bottom-most ply 7, is a sheet of liquid-impervious material. A suitable liquid-impervious material is a product manufactured and sold as breathable perforated PE Film by Berry Plastics having a business address at 349 Taylor Industrial Road, McAlester, Okla. 74501. The collapsed pad and each ply have the same configuration as the composite substrate 10.

As described herein, the invention provides an effective means of preventing soiling of under garments and outer clothing by bodily fluids, most notably blood, issuing from the crotch region of individuals.

Many variations and modifications may be made to the above-described embodiments without departing from the scope of the claims. All such modifications, combinations, and variations are included herein by the scope of this disclosure and the following claims. For example, although the invention has been described in the context of managing blood flow from a menstrual issue, it can also be used to inhibit seepage of urine or other liquid discharges from the crotch region of an individual whether female or male.

The invention claimed is:

1. A composite liquid-retentive substrate for a hygiene article, the composite liquid-retentive substrate comprising:
   a substantially elongated base layer comprising first liquid-absorptive material having a posterior end having a longitudinal-most posterior edge, inwardly-approaching posterior side edges and opposing posterior corners, an anterior end smaller than and diametrically-opposed to said posterior end having a longitudinal-most anterior edge, inwardly-approaching anterior side edges and opposing anterior corners, and
   an intermediate tapered region interconnecting said posterior end and said anterior end; and
   at least one of
      a posterior liquid-flow abutment comprising second absorptive material disposed around a perimeter of said posterior end including said posterior corners extending to an open apex proximate said intermediate tapered region thereby resulting in a wide-based, narrow-opening, triangle in which said open apex faces said intermediate tapered region; and
   at least one
      substantially triangular-shaped anterior liquid-flow abutment separate and distinct from said posterior liquid-flow abutment comprising said second absorptive material wherein each of said substantially triangular-shaped anterior abutments is disposed at only one of said anterior corners of said anterior end.

2. The composite liquid-retentive substrate of claim 1, wherein said anterior liquid-flow abutment comprises an anterior liquid-flow abutment disposed at each of opposing said anterior corners.

3. The composite liquid-retentive substrate of claim 1, wherein said intermediate tapered region is adapted for alignment with leg openings of a pair of underpants.

* * * * *